(12) United States Patent
Ur et al.

(10) Patent No.: US 12,088,492 B2
(45) Date of Patent: Sep. 10, 2024

(54) COMPUTERIZED SYSTEM AND METHOD FOR DETERMINATION OF DESTINATIONS FOR COMPUTER NETWORK REQUESTS

(71) Applicant: SOURCE Ltd., Valletta (MT)

(72) Inventors: Shmuel Ur, Shorashim (IL); Lova Pogosov, Haifa (IL)

(73) Assignee: SOURCE Ltd., Valletta (MT)

( * ) Notice: Subject to any disclaimer, the term of this patent is extended or adjusted under 35 U.S.C. 154(b) by 0 days.

(21) Appl. No.: 17/859,417

(22) Filed: Jul. 7, 2022

(65) Prior Publication Data

US 2024/0015090 A1    Jan. 11, 2024

(51) Int. Cl.
*H04L 45/122*    (2022.01)
*H04L 43/062*    (2022.01)
*H04L 45/28*    (2022.01)
*H04L 45/42*    (2022.01)

(52) U.S. Cl.
CPC .......... *H04L 45/122* (2013.01); *H04L 43/062* (2013.01); *H04L 45/28* (2013.01); *H04L 45/42* (2013.01)

(58) Field of Classification Search
None
See application file for complete search history.

(56) References Cited

U.S. PATENT DOCUMENTS

| | | | |
|---|---|---|---|
| 9,374,454 B1 * | 6/2016 | Davis | H04M 3/42102 |
| 9,832,126 B1 * | 11/2017 | Davis | H04M 3/367 |
| 10,320,680 B1 | 6/2019 | Mehr | |
| 2009/0313043 A1 | 12/2009 | Schoenberg | |
| 2010/0036837 A1 * | 2/2010 | Ando | G06Q 10/00 707/706 |
| 2020/0045131 A1 * | 2/2020 | Nigam | H04L 67/54 |
| 2021/0049657 A1 | 2/2021 | Mimran | |

OTHER PUBLICATIONS

Hu, "Peer-to-Peer Data Dissemination for Deadline-Sensitive Streaming in VANETs", Jan. 1, 2020, IEEE, IEEE Access (vol. 8, pp. 136348-136360) (Year: 2020).*
Alok R Chaturvedi, et al., "Issues in Server Farm Design for Real Time E-Commerce Transactions", Jan. 2001, Source Re PEc.
International Search Report and Written Opinion for PCT Patent Application No. PCT/EP2022/069795 dated Mar. 3, 2023.

* cited by examiner

*Primary Examiner* — Davoud A Zand
(74) *Attorney, Agent, or Firm* — PEARL COHEN ZEDEK LATZER BARATZ LLP

(57) ABSTRACT

A system and method may service and manage the lifecycle of computer network requests by a gate node. Using one or more computers and/or computer processors, embodiments may allow managing network requests and replies, including performing a variety of related operations, such as extracting information from network requests and replies, receiving a computer network request from a remote computer or sender address; determining a subset of remote destinations to service the request based on information stored in the gate; sending the request to a plurality of transactee sites over a data network; processing received replies and/or information stored in gate's memory; preparing and sending an updated reply to the sender or transactor; and so forth. Embodiments may allow determining or changing, from a set of available destination determination and/or reply management schemes, a particular scheme for a given network request (e.g., at a given timeslot) based on information stored in gate's memory.

18 Claims, 6 Drawing Sheets

COMPUTERIZED SYSTEM AND METHOD FOR DETERMINATION OF DESTINATIONS FOR COMPUTER NETWORK REQUESTS

FIELD OF THE INVENTION

The present invention relates generally to the determining of destinations and management of network-based requests by a third-party server, such as a "gate".

BACKGROUND OF THE INVENTION

Web-based communication between computer systems may involve sending requests by a transactor (e.g., a requestor of data, or a customer), and receiving replies from a transactee (e.g., a service provider, a streaming server, etc.). In addition to their contents, which may correspond to particular service and/or transaction details (e.g., for placing an order for a certain product at a vendor's website; or for asking for a program to be run at a remote server), requests may include sender information, such as address, location, and the like. In many contexts—e.g., where control over the determining the destinations for requests is desired, for instance, in case where some potential destinations are to be avoided, or in case where actively managing network traffic is desirable.

SUMMARY OF THE INVENTION

A system and method may service and manage the lifecycle of computer data network requests by a dedicated computer systems known as a gate. Using one or more computers and/or computer processors, embodiments may allow for example extracting a plurality of information items or computer data from network requests and replies, as well as storing information items describing a plurality of network requests, in addition to potential senders and potential destinations for such requests (which may include for example a set of remote computer addresses), in gate's memory. Embodiments may allow for example performing one or more of: receiving, by a gate, a computer network request from a remote computer or sender address, belonging to e.g., a human user, or an automated computer system (e.g., a bot) configured to send network requests; searching for a plurality of potential remote destinations or transactees to service the request; determining a subset of one or more remote destinations to service the request based on information stored in the gate; routing the request to the destinations determined for the request; sending the routed request to a plurality of transactee sites over a data network; receiving replies from different transactees; processing received replies and/or information stored in gate's memory; preparing and sending an updated reply to the sender or transactor; and preparing and sending reports to transactees, describing for example the receiving of their replies, as well as responses and further actions involving, e.g., interactions between the transactor and a plurality of transactees (which may or may not be limited to computer actions, but also for example include performing a service or providing a product by a transactee).

Embodiments of the invention may allow determining, choosing, or changing, from a set of available destination determination and/or reply management schemes, a particular scheme for a given network request (for example at a given timeslot) based on information items stored in gate's memory.

BRIEF DESCRIPTION OF THE DRAWINGS

Non-limiting examples of embodiments of the disclosure are described below with reference to figures attached hereto that are listed following this paragraph. Identical features that appear in more than one figure are generally labeled with the same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining,"

"establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items.

Unless explicitly stated, the method embodiments described herein are not constrained to a particular order in time or to a chronological sequence. Additionally, some of the described method elements can occur, or be performed, simultaneously, at the same point in time, or concurrently. Some of the described method elements may be skipped, or they may be repeated, during a sequence of operations of a method.

Figure 1:
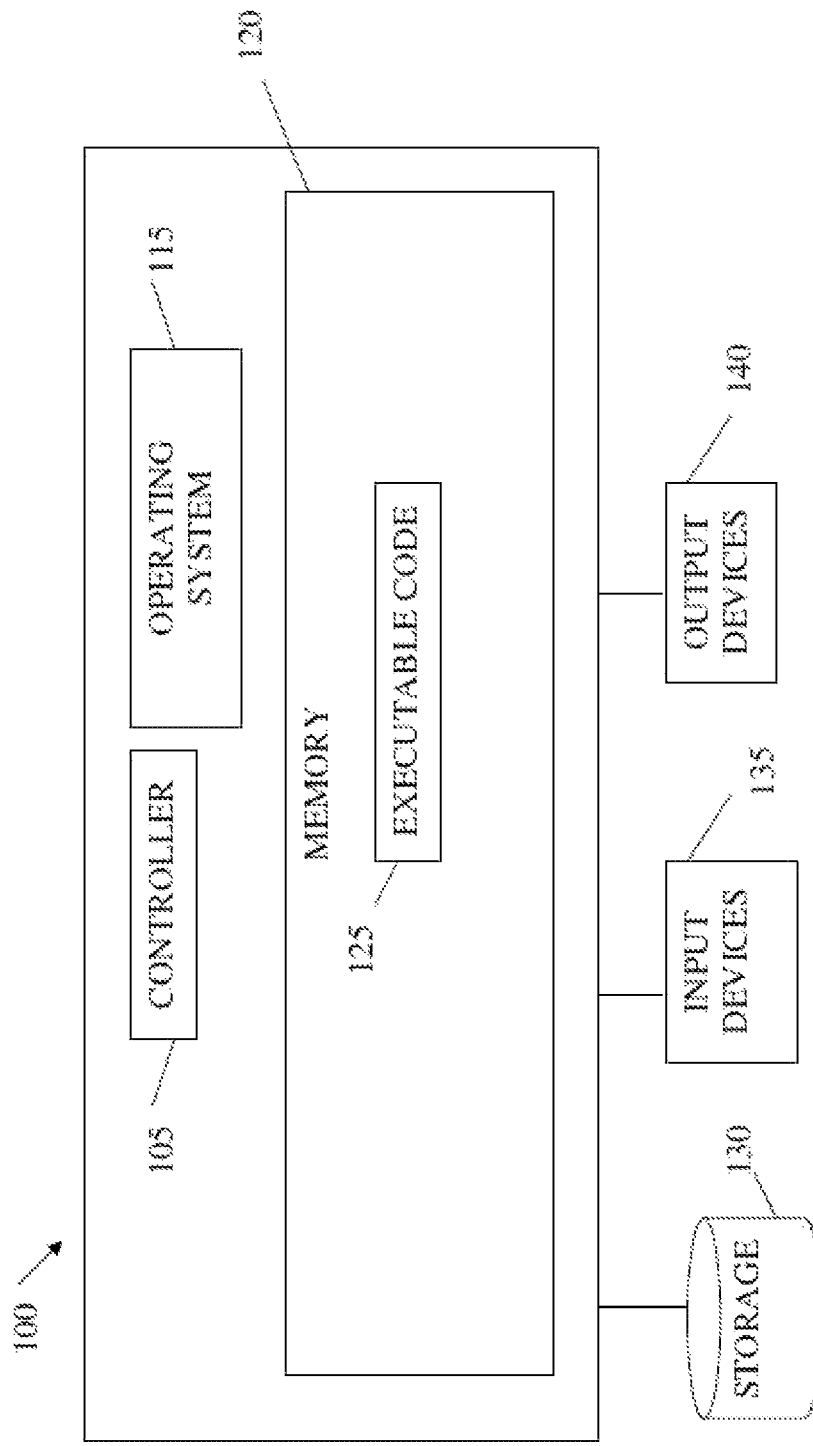
FIG. 1 shows a block diagram of a computing device according to illustrative embodiments of the present invention.

Reference is made to FIG. 1, showing a non-limiting, block diagram of a computing device or system 100 that may be used for destination determination of routing requests according to some embodiments of the present invention. Computing device 100 may include a controller 105 that may a hardware controller. For example, computer hardware processor or hardware controller 105 may be, or may include, a central processing unit processor (CPU), a chip or any suitable computing or computational device. Computing system 100 may include a memory 120, executable code 125, a storage system 130 and input/output (I/O) components 135 and 140, respectively. Controller 105 (or one or more controllers or processors, possibly across multiple units or devices) may be configured (e.g., by executing software or code) to carry out methods described herein, and/or to execute or act as the various modules, units, etc., for example by executing software or by using dedicated circuitry. More than one computing devices 100 may be included in, and one or more computing devices 100 may be, or act as the components of, a system according to some embodiments of the invention.

Memory 120 may be a hardware memory. For example, memory 120 may be, or may include machine-readable media for storing software e.g., a Random-Access Memory (RAM), a read only memory (ROM), a memory chip, a Flash memory, a volatile and/or non-volatile memory or other suitable memory units or storage units. Memory 120 may be or may include a plurality of, possibly different memory units. Memory 120 may be a computer or processor non-transitory readable medium, or a computer non-transitory storage medium, e.g., a RAM. Some embodiments may include a non-transitory storage medium having stored thereon instructions which when executed cause the processor to carry out methods disclosed herein.

Executable code 125 may be an application, a program, a process, task or script. A program, application or software as referred to herein may be any type of instructions, e.g., firmware, middleware, microcode, hardware description language etc. that, when executed by one or more hardware processors or controllers 105, cause a processing system or device (e.g., system 100) to perform the various functions described herein.

Executable code 125 may be executed by controller 105 possibly under control of an operating system. For example, executable code 125, controller 105 and/or system 100 may be an application that requests a computer network transaction, services such a transaction, or acts as an intermediary or gate, as further described herein. Although, for the sake of clarity, a single item of executable code 125 is shown in FIG. 1, a system according to some embodiments of the invention may include a plurality of executable code segments similar to executable code 125 that may be loaded into memory 120 and cause controller 105 to carry out methods described herein.

Storage system 130 may be or may include, for example, a hard disk drive, a CD-Recordable (CD-R) drive, a Blu-ray disk (BD), a universal serial bus (USB) device or other suitable removable and/or fixed storage unit. In some embodiments, for example, when included in a mobile communication device such as a smartphone or laptop computer, storage system may be a memory, e.g., a flash memory or a solid state disk (SSD).

Input components 135 may be, may include, or they may be used for connecting (e.g., via included ports): a mouse; a keyboard; a touch screen or pad or any suitable input device. Output components 140 may include one or more screens, touchscreens, displays or monitors, speakers and/or any other suitable output devices. Any applicable I/O components may be connected to computing device 100 as I/O components 135 and 140, for example, a wired or wireless network interface card (NIC), a universal serial bus (USB) device or an external hard drive.

A system according to some embodiments of the invention may include components such as, but not limited to, a plurality of central processing units (CPU) or any other suitable multi-purpose or specific processors, controllers, microprocessors, microcontrollers, field programmable gate arrays (FPGAs), programmable logic devices (PLDs) or application-specific integrated circuits (ASIC). A system according to some embodiments of the invention may include a plurality of input units, a plurality of output units, a plurality of memory units, and a plurality of storage units. A system may additionally include other suitable hardware components and/or software components. In some embodiments, a system may include or may be, for example, a personal computer, a desktop computer, a laptop computer, a workstation, a server computer, a network device, or any other suitable computing device.

A computer data network as described herein may be, may comprise or may be part of a private or public Internet Protocol (IP) network, or the internet, or a combination thereof. Additionally or alternatively, a computer network may be, comprise or be part of a global system for mobile communications (GSM) network. For example, network may include an IP network such as the internet, a GSM related network and any equipment for bridging or otherwise connecting such networks as known in the art. In addition, network may be, may be part of an integrated services digital network (ISDN), a public switched telephone network (PSTN), a public or private data network, a local area network (LAN), a metropolitan area network (MAN), a wide area network (WAN), a wireline or wireless network, a local, regional, or global communication network, a satellite communication network, a cellular communication network, any combination of the preceding and/or any other suitable communication means. Accordingly, numerous elements of network are implied but not shown, e.g., access points, base stations, communication satellites, GPS satellites, routers, telephone switches, etc. It will be recognized that embodiments of the invention are not limited by the nature of network.

In some embodiments of the invention, the sending of requests by a transactor to a given destination or transactee (note that the terms destination and transactee and/or their combination may be used interchangeably in the context of the present disclosure), or a plurality of transactees, may be mediated by a separate, third-party unit or remote computer, otherwise known as a "gate". Generally speaking, a given transactor, or transactee, or a gate may correspond to (e.g. be using and/or operating and/or be represented by) a computing system connected to a data network. In other words, the transactor/transactee should be, or should operate, a computer system such as for example system 100 herein. Upon receiving a given request from a transactor, the gate may determine, according to predefined rules and policies, a particular destination transactee to which the request may be sent. Determining a destination by the gate may thus generally involve taking different sources and items of information into account (e.g., timestamps of sent requests) in order to achieve desired communication and transaction activity patterns (e.g., ones satisfying a given load-balancing policy or conditions/criteria as explained herein).

Embodiments of the invention may allow storing or including, by a gate, a plurality of information items on a plurality of users (which may be transactors or transactees as described below) which may be or may have been involved in network transactions; receiving a computer network request from a remote computer, belonging to for example a human user, transactor, or sender; searching for a plurality of potential remote destinations to service the request; determining a subset of one or more remote destinations to service the request; routing the request to transactee sites (e.g., using an appropriate destination determination and reply management procedure); sending the routed request to a plurality of transactee sites over a data network; receiving replies from different transactees; processing received replies; preparing and sending an updated reply to the transactor; and preparing and sending reports to transactees, describing the receiving of their replies.

Embodiments of the invention may allow determining, choosing, or changing, from a set of available destination determination and reply management schemes, a particular scheme for a given network request at a given timeslot.

Each of the actions and/or stages included in the management of network request(s) by the gate may (which may be for example receiving a network request, determining of the one or more destinations, routing of the request, sending of the request, sending of an updated reply, and sending of one or more of the responses, as well as determining a destination determination scheme for a given request) generally be set or determined by the stored information items.

Embodiments of the invention may generally be used for the servicing of computer data network requests by a dedicated computing device, and/or system, and/or entity (referred to as the "gate" herein). The streaming of a video file and the request for a given health service using and including digital data from a health service provider (which may be, for instance, a health maintenance organization) will be used as a general example herein, although such examples should be understood as non-limiting. Those skilled in the art would recognize that various kinds of network requests and corresponding services may be used in different embodiments of the invention. In the context of such examples, it should be noted that the gate, as well as the transactor and the transactees (service providers such as doctors having a contract with a health management organization, a video streaming service, and so forth) may be or may operate computer systems such as system 100 considered herein—and that the plurality of computing systems may be connected by a data network as described herein.

In general, a transactor may contact and/or communicate with the gate using for example cellular data over a data network. Communication with the gate may be performed, for instance, using a dedicated application on a mobile phone or personal computer. Various alternative communication procedures and standards known in the art may be used in different embodiments of the invention in order to receive a given network request by the gate. In some embodiments, a gate is configured to handle or manage requests from a plurality of transactors, for example belonging to a predefined pool of users (which may be for example defined by a list or a table of user addresses; other items, forms or sources of information may be used in different embodiments), or identified by particular details (for example specific geographic location, such as a city or district; belonging to a specific age group, such as between 20-40 years old; as well as user-defined characteristics or preferences. Examples of information or details used to define the transactors should be considered as non-limiting). In some embodiments, the gate may include or possess information on each user it is configured to service; a gate used by a health management organization (HMO) may incorporate for example user or client information such as age, gender, living address and contact details, medical file and history (including, e.g., prescribed medications, past treatments, diagnoses, etc.), past services requested by the client, details of clinicians who treater the user as a patient, user-defined preferences (for example "contact using provided email address instead of via phone", "only suggest services provided within a radius of X kilometers from living address", etc.), and the like.

The gate may also include or possess for example similar information regarding a plurality of service providers, which may be potential transactees and/or destinations to which a request by a given user may be sent. Thus, the gate may include items of information on a plurality of clinicians (e.g., cardiologists, psychiatrists, endocrinologists, and the like, which may operate computer systems as discussed herein—as well as clinic geographic locations, a set of services they may provide and their service hours, fees, and so forth) which may be contacted according to requests by clients or transactors who are to be serviced by the gate. In some embodiments, service providers or transactees may contact the gate to provide or update details and/or information kept and/or managed by the gate. By way of illustration, a doctor such as a cardiologist may, as a potential transactee, update the gate with a new clinic address, operating hours, a set of provided services, and workflow preferences (e.g., that upon agreeing to service a given a network request for a service by a given user or HMO client, the latter may be asked to directly contact the doctor in order to provide further details regardless of information already existing in the system), for example via the network and using a computing system (such as for example system 100). It should be noted that terms such as 'information', 'metadata', and 'parameters', may be synonymous with 'information items' (designating, for instance, finite information collected or stored at a particular point in time, and in a particular data format) in the context of the present description.

In some embodiments, user and/or service provider (which may be considered as transactor and transactee, for example, with reference to a given network transaction and corresponding request by the transactor) information items (describing e.g. a plurality of computer network requests, potential senders, and potential remote destinations for such requests, and historical details of network requests and corresponding replies and/or responses, as further described herein) may be stored in a dedicated database within the gate's memory resources (for example memory 120 in computer system 100). In other embodiments, such a database may itself be stored for example in a memory unit of a remote computer or on memory resources provided via cloud services and accessed through the web (which may be for example a cellular data network). Alternative schemes for storing information and corresponding database may be used in various embodiments of the invention.

Using gate-based communication for the servicing of network requests, a given user or transactor may be agnostic to particular service providers which may be known to, and further contacted by, the gate. Embodiments of the invention may store information describing, for example, a plurality of transactors or potential senders of network requests, a plurality of transactees or potential remote destinations to service a given network request, and additional information items describing a plurality of additional network requests—for example recorded historical details or details associated with the history of computer network requests, including various events recorded throughout their lifecycle (e.g., time of receiving a given request by the gate, times of sending the request to a plurality of transactees, replies received for the request, responses to each of the replies, and so forth—in accordance with the present disclosure. As a non-limiting example, see discussion regarding the calculation of success rates herein). Again, using the HMO example described herein, the gate may for example include and/or have access to a database containing a set of medical practitioners (which may be considered as transactees or potential transactees and may operate computing systems such as for example system 100, to offer a variety of services), and to a database containing data describing a set of patients (which may correspond to the set of transactors known to the gate which may similarly operate computing systems such as for example system 100). A non-limiting illustration of such databases may, for example, be seen in Tables 1-2 (note that the two tables are provided as examples, and should not be understood as completing each other; Table 1 describes a set of cardiologists located in New York City (NYC) while Table 2 describes a set of patients belonging to different HMOs operating and found in the same area).

A client may for instance notify or inform the gate of an emergency (such as, e.g., a heart attack) while the client is located for example in the financial district, Manhattan; in such an example scenario, a monitoring device connected to the network may interact with a communication device connected to the network such that when an emergency is detected or measured the gate may be contacted immediately and automatically) and the gate may automatically choose the appropriate service (and thus network node) included in the database that may be requested from appropriate transactees and/or destinations (each operating or being a network node) based on client and service provider information (for example an evacuation to a nearby emergency unit which has a contract with the HMO—e.g., entry no. 2 in Table 1—for example found closest to the location of the relevant patient, e.g., patient no. 2 in Table 2, who may send a request for an emergency unit service; see also next paragraph in the description). Additional non-limiting example cases referring to HMO-based users and service providers (which may be considered as transactors and transactees in the context of the present invention) are further described herein.

Embodiments of the invention may thus include information items regarding possible users or transactors that may contact the gate (e.g., sending requests to be serviced by the latter). In this context, users or transactors may be listed or stored in a table or database in the gate's memory (e.g., memory 120 in computer system 100), for example in cases where the set of transactors that may request for services is fixed or predetermined. In some embodiments, the gate may be configured to receive and/or update the set of transactors and corresponding stored information in specific time intervals, while in other embodiments such set of users and information may be manually provided to the gate by a human operator. Different approaches for establishing an appropriate database or alternative data structure for storing user or transactor details are known in the art. Using the HMO example described herein, transactor detail information may for example be organized in a table such as Table 2.

TABLE 1

| No. | Practitioner Name/ID | Service Type | Location | Opening hours ... | Home services | Accessible | Rating Score |
|---|---|---|---|---|---|---|---|
| 1. | Dr. John Doe [00101] | cardiologists | 600 E 32$^{nd}$ St., Manhattan, NYC | Monday, Wednesday, Friday from 15:30 pm-19:00 pm | Yes | No | 87.3 |
| 2. | Presbyterian Lower Manhattan Hospital [00102] | Emergency Room | 833 Gold St., Manhattan, NYC | Every day, all hours ... | No | Yes | 93.9 |
| ... ... | ... | ... | ... | ... | | | |

TABLE 2

| No. | Patient name/ID | Gender | Age | Address | Service level agreement (SLA) with the HMO | Medical history Accessible | Medical history records | HMO the transactor belongs to |
|---|---|---|---|---|---|---|---|---|
| 1. | Sam Dok [03021] | Male | 27 | 104 22$^{nd}$ St, apt. 24, Manhattan, NYC | Gold | N | File (or link to a file) including all medical history | A |
| 2. | Joan Femont [04932] | Female | 51 | 98 Washington Ave., apt. 8, Brooklyn, NYC | Silver | Y | File (or link to a file) including all medical history | B and C |
| ... | ... | ... | ... | ... | | | | |

In the example used in Table 2, a file including a transactor's medical history may be for example a text file or table comprising various fields, which may or may not be human readable e.g.

Sam Dok [03021]
  BloodTest 280922022
    Hem: 4.3
      TriGlic: 809
  HrtARisk: 8
  PsychDiag: SCZ
  PerscMed: PER03, OLA77, BZD08

Embodiments may thus use data and/or information stored by the gate in order to for example automatically choose a plurality of destinations for a network request by a given transactor and automatically respond to a plurality of replies.

Current systems and methods of destination determination for network requests by, e.g., a gate, do not provide the sender or transactor with information regarding offers from potential providers or transactees which have not been chosen to service the request. In such manner, the transactor remains agnostic to the destination determination process and to the chosen destinations associated or potentially associated with it. Embodiments of the invention may improve such technology and provide such information in, e.g., updated replies and reports as further explained herein. In such manner, transactors may collect information that may be used for further optimization and/or improvement of future orders and requests—which may, for example, be first sent to transactees shown to be preferred based on past performance and/or servicing of appropriate requests, and for example based on a corresponding success rate and probability of success as further described herein. Further, current systems and methods for destination determination of network requests employ a single, predefined destination determination scheme, characterized by an unmodifiable and inflexible workflow—which may include, for example, using the gate for either sending network requests to destination transactees or back to the transactor's sending address (such that the gate is not involved in sending the request to transactees). Embodiments of the invention may allow setting, determining or changing a destination determination scheme based on stored information, such as request parameters, data or metadata, such that a particular workflow may be chosen for a given request in order, for example, to optimize the gate's performance, capacity, and processing capabilities—or in order to respond to network load-balancing considerations. Embodiments of the invention may also enable distinguishing between different transactors, transactees and transactions based on such information items, parameters, data and metadata associated with them—such that different destination determination procedures and associated workflows for servicing the corresponding network requests may be tailored for transactors, transactees and transactions of different types. Embodiments of the invention may therefore improve current systems and methods known in the art by for example enabling a faster and more efficient management of network requests sent or transmitted over a data network. This may be achieved for example by substantially reducing the number of times a given request has to be sent or transmitted over the network (for example from a transactor to different transactees, and/or from transactees to a transactor, and/or from a transactor/transactee to a gate). Based on data-driven, adaptable and focused network request management procedures as outlined herein (e.g., employing success rates and/or probabilities of success as part of the destination determination for the network request), a given network request may be successfully serviced by a given transactee or a plurality of transactees while being sent or transmitted fewer times over the network than in prior art approaches. As a result, the overall network traffic may be reduced over the network space spanning a plurality of computing systems operated by the relevant transactors, transactees, and gate. Furthermore, the number of sendings or transmissions over the network may itself be documented, for example as information items described in a database and including request management history details (such as for example a table similar to Table 3 herein)—which may help predicting network traffic and, consequently, enable more adaptive network traffic management which may for example respond to real-time data, may ensure or enforce desirable load balancing, and may prevent related network failures and errors.

Thus, a gate as referred to herein may or may not include information items and/or data describing a predetermined set of transactees or destinations which may be chosen to service the request. One non-limiting example to be used throughout the present document is that of an interaction between a HMO and one of its clients. In such interaction, the client or user may access and communicate with the gate using a personal computer device having an active internet connection. The gate may accordingly be a mediating entity connecting the user to a given service provider. It may for example handle or service a plurality of users—for example those belonging to a specific city or district, clients of a specific HMO, and patients belonging to a particular health-risk group (e.g., senior citizens at the age of 65 and above), clients having a particular contract or service level agreement with the organization (SLA; for example platinum membership in the HMO), and so forth—in accordance with the discussion herein (e.g., as reflected in information and/or information items stored in a dataset similar to entries found in Table 1). Various criteria for being serviced or handled by a particular gate may be included in different embodiments of the invention.

Some embodiments may include one or more business rules engines (BREs) implemented in the gate which allow formulating logical constraints on handling network data structures and databases such as those illustrated in Tables 1-3, and as further demonstrated herein. Those skilled in the art would recognize, however, that examples including, e.g., requests by HMO clients for services associated with health service providers are merely used in a non-limiting manner—and that alternative embodiments of the invention may be applied in substantially different contexts where a different kind of transactors and transactees is considered, and where mediation and management of network requests by the gate may be executed in for example a plurality of different network request management schemes, e.g., as further explained herein. In some embodiments, request parameters may be used or considered using BREs as part of destination determination procedures, such as for example as further discussed herein.

TABLE 3

| No. | Request ID | Sending time | Time of arrival at gate | Urgency level | Request specifications | Request type | Serviced_by (Completed?) |
|---|---|---|---|---|---|---|---|
| 1. | [300001] | 20:20:31 | 20:20:35 | High | File or link to a file including request details chosen by transactor | Appointment | [00101] (No) |
| 2. | [300002] | 21:33:45 | 22:30:01 | Medium | File or link to a file as above. | Medical file review | — |
| ... | ... | ... | ... | ... | ... | ... | ... | requests during different stages of their lifecycle based on request parameters, data and/or metadata. Request information or metadata which may be received by the gate may generally include, for instance, a given request's or client's SLA; parameters or data describing times of occurrence of different communication events along its lifecycle (e.g., timestamps of sending the request by a transactor; of receiving one or more replies from a transactee; and of destination determinations by a gate—as well as geographic locations, and security permissions associated with such events); as well as various additional parameters such as language preferences and historical information and/or data. Additional metadata and/or information may be used in other embodiments of the invention. In addition, request data and/or metadata may include auxiliary information from various sources, such as output provided by a search engine, location information regarding the sending address of the transactor or the destination transactees, and information regarding the particular transaction or request (e.g., a movie name for which a video file is requested, and/or the format requested for the file; a particular health service request such as an appointment with a certain type of specialist such as a cardiologist; such information may include a general type of software-as-a-service which may be involved in servicing the request under consideration; in this context, all examples should be considered as non-limiting).

In this context, embodiments of the invention may for example include storing request parameters, and/or data, and/or metadata and/or history information in a dedicated database, which may for example be organized as a table. An example such database is illustrated in Table 3. Destination determination and appropriate responses for a given request by the gate may thus be based on for example a plurality of In some embodiments of the invention, an SLA for a given transactor may reflect for example sensitivity to certain factors and/or features in the requested service which may be taken into account by the relevant BRE in the context of determining a destination to service the transactor's network request. Thus, an SLA may or may not reflect, for example, a given transactor's sensitivity to the cost of the service requested. In such case (which is merely a non-limiting example), a low SLA may be interpreted by a given BRE such that the servicing option of the lowest cost (or a plurality of lowest-cost options) should be chosen as a given request's destination among a plurality of alternative options involving varying costs, e.g., that cost considerations should be taken as a primary factor in the destination determination process—while a high SLA may interpreted as indicative of relative indifference toward cost considerations and a higher sensitivity towards quality considerations (which may for example be reflected in past ratings by clients, which may themselves be stored in the gate's memory—for example as additional fields in a database or a history file such as the one illustrated in Tables 1-2; see also practical example in Procedure I herein).

Figure 2:
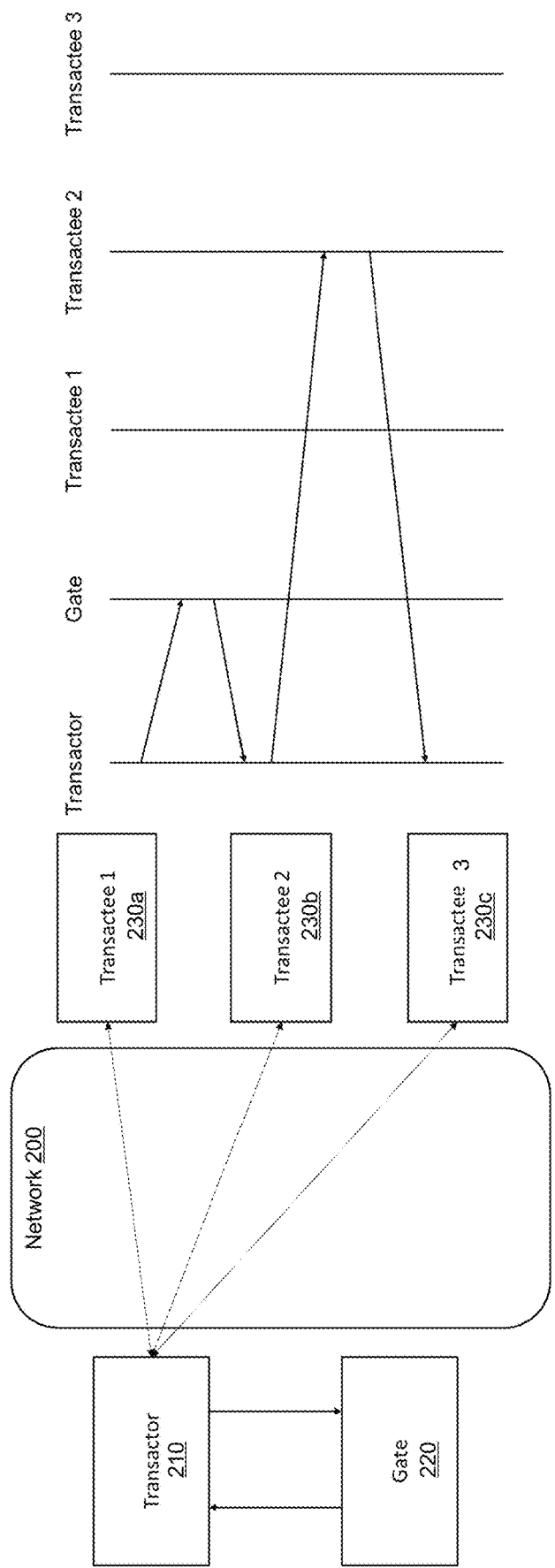
FIG. 2 shows an overview of a system and method of determining destinations for network requests (scheme "A") according to one embodiment of the present invention.
Figure 3:
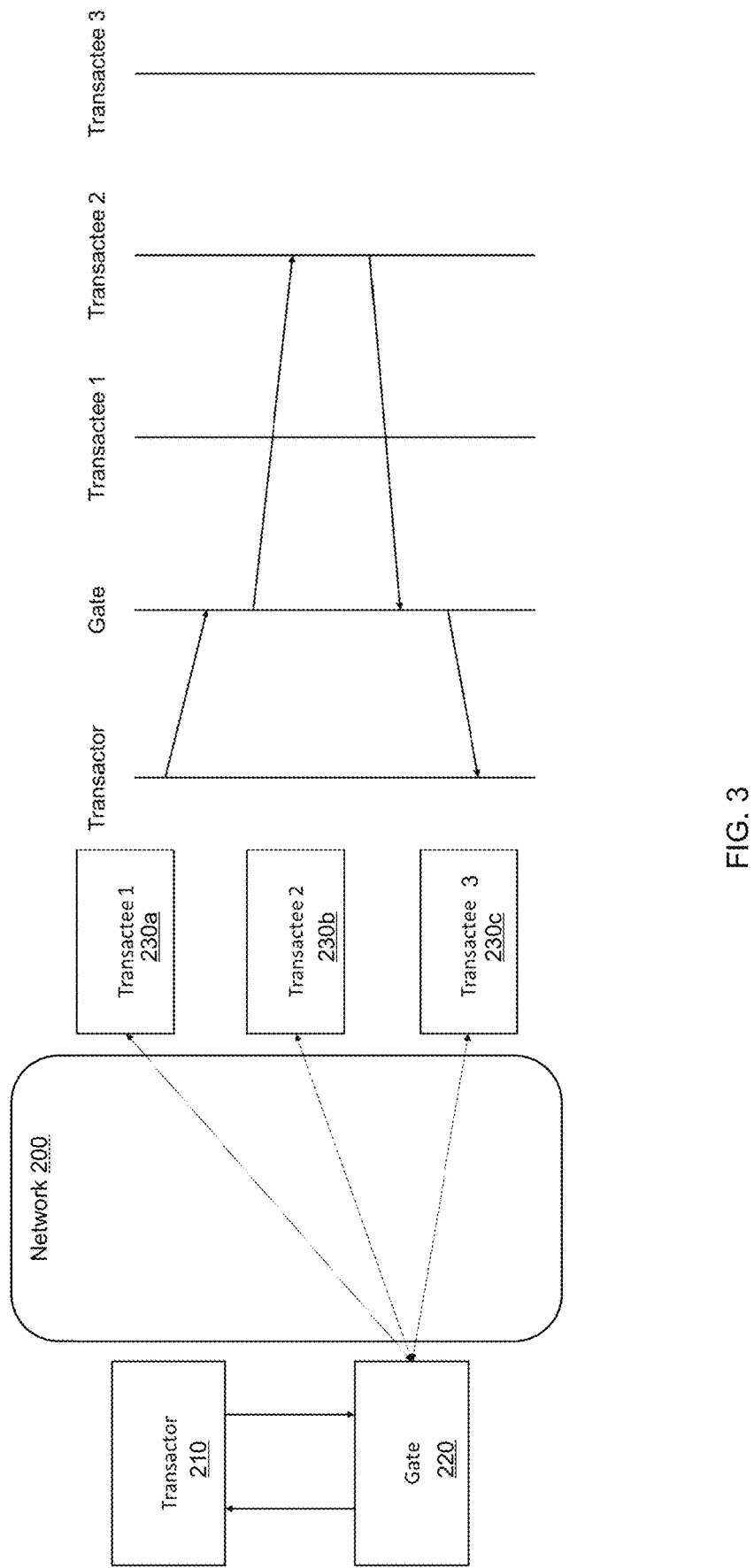
FIG. 3 shows an overview of a system and method of determining destinations for network requests (scheme "B") according to another, different embodiment of the present invention.
Figure 4:
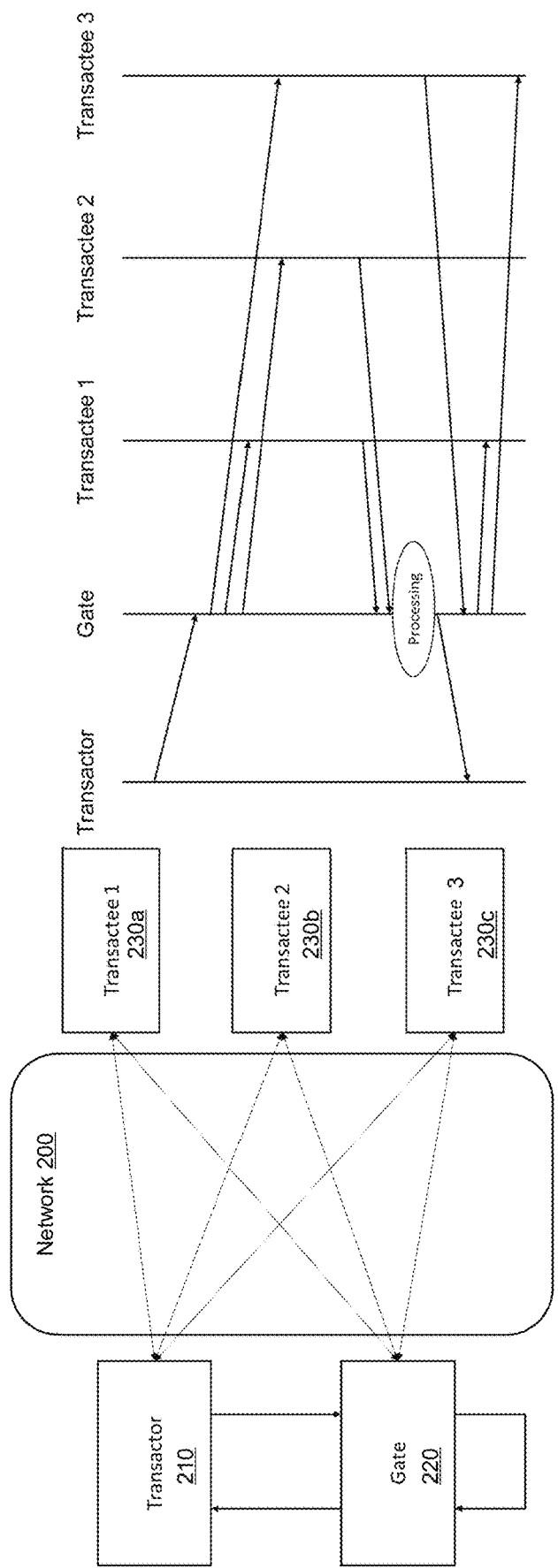
FIG. 4 shows an overview of a system and method of determining destinations for network requests (scheme "C") according to illustrative embodiments of the present invention.

Embodiments of the invention may set or determine a plurality of destinations for a given request, for example based on information items stored in the gate's memory as described herein. A given destination determination may be represented using, or based on, for example a computer data network structure, where nodes are computer systems and may correspond to computer addresses involved or chosen as destinations (e.g., both transactor sending address and destination transactee addresses). Example such representations are illustrated in FIGS. 2-4. Arrows crossing network 200 represent a determination or association of a given request by transactor 210 with transactees 230a-c which may be or may operate computing systems such as for example system 100 (see also additional reference to FIG. 5 herein, in the context of choosing a destination determination scheme for a network request). The determination of destinations (e.g. based on information items such as for example demonstrated herein) may thus allow a network request to be sent to the destinations chosen for it, and for example to be returned or sent back to its sending address once the request has been serviced. Alternative representations of destination determinations offered by embodiments of the invention may also be used (e.g., tables, lists, etc.)

Given a set of potential target transactees, which may be for instance predefined and included in the gate's memory (e.g., stored as a plurality of information items such as for example a list or table such as Table 1, which may or may not be part of a larger database; alternative data structures may be used in various embodiments) embodiments of the invention may allow determining a subset of transactee addresses, or destinations, to which a given network request may be sent. Particular destinations within a subset may be chosen based on various rules implemented in an appropriate BRE. In accordance with preceding example cases herein, a client of an HMO located in lower Manhattan (information and/or information items regarding the location of the client or potential sender of network requests may be stored in the gate for example according to the format shown in Table 2) may for example request, at 16:00 on a Thursday, a general, periodic inspection (which may not include for example a particular intervention or test from the doctor) by a cardiologist to take place as soon as possible. Embodiments of the invention may, for example using a first BRE, determine a subset of cardiologists among the overall set of cardiologists working with the HMO under consideration, a subset of cardiologists within a predetermined geographic distance from the user or transactor (for example the subset of cardiologist clinics found in Manhattan, which may be assumed to be accessible to the user). A second BRE may be used to further determine a subset of cardiologist clinics for which service hours match the user's preferences (for example between 16:00-19:00 the user may define such preferences manually, for instance using an app provided by the HMO). A third BRE may be used to further determine a subset of cardiologist clinics for which the fee for the requested service is below a predetermined threshold (for example 300 USD). The subset of cardiologist clinics satisfying the criteria enforced by the three aforementioned BREs may consist for example of five clinics, which may be chosen as potential destinations or transactees to service the user's request.

In some embodiments, the gate may be configured to check or measure the load balancing, or a state of network traffic to particular destinations among the set of potential transactess. This may be achieved, for instance, by sending an echo request or ping by the gate to remote locations or destinations (e.g., following the receiving of a corresponding network request, and before the routing or sending of the request to destination transactees) and receiving one or more replies from which load scores may be derived, measured, or calculated (alternatively the gate may request such information and/or information items from for example a given transactee using a dedicated Application Programming Interface (API), which may be configured to provide such information items upon request). In such manner, the gate may compare load scores among different potential transactees or remote destinations and choose the destination for which the "lightest" load trafficking was calculated (for example such that the request may reach its destination address in the shortest time possible). Other methods of measuring network and/or communication trafficking are known in the art, and may be used in alternative embodiments of the invention. In some embodiments, a load trafficking score may be calculated for a given transactee or potential destination. An example calculation of such score may for instance comprise the amount of time required for a given transactee, which may be or may operate for example a computing system such as e.g. system 100, to respond to the ping request and the time it takes for the latter to reach the gate; a percentage of ping requests returned within a time frame or below a predetermined threshold; a weighted average of timings and percentages such as the latter, and so forth. Calculated scores or network trafficking information may be stored and/or updated in a database such as demonstrated in Table 1. In some embodiments, network trafficking information or scores may be measured, calculated, or updated periodically—for example in order to have robust and reliable assessments of the current trafficking state at a given destination which may be chosen to service the request. In other embodiments, multiple measurements or calculations (e.g., employing a trafficking score as demonstrated herein) of network trafficking information may be used to construct or train a predictive model of network trafficking properties; various machine-learning and artificial neural network models may be used for this purpose as known in the art. Embodiments may therefore use predictions by such models—which may themselves be stored in a dedicated database (for example such as that illustrated in Table 1) in order to determine a subset of preferred transactees or destinations to service a given network request.

Some embodiments of the invention may thus employ BREs and accordingly determine, for a given network request, the subset of destinations for which network traffic is least significant (e.g., in order to ensure that the request arrives at the destinations at an optimal time) or expected to be least significant at a specific timeslot (which represents, e.g., present or future point in time). To such end, embodiments may rank or sort potential transactees according to trafficking scores calculated as described herein (for example, the transactee for which the smallest trafficking score, corresponding to the shortest response time to a ping request, was calculated may be ranked as #1; the transactee for which the second smallest such score was calculated may be ranked as #2, and so forth). Once such ranking or sorting is achieved, embodiments may for example choose the highest ranked candidate (e.g., for which network or communication traffic is predicted to be the least significant) as a destination for the network request under consideration. Additional rules that may be incorporated into BREs may include choosing a destination based on, e.g., a SLA for a transactor or transactee (for instance, for a transactor with a "low" SLA—the BRE may choose the transactee offering the least costly service option—e.g., a doctor's clinic offering the least costly option for the requested service (for example when patient or transactor details or information indicate high sensitivity to the cost of the requested service, e.g., which may be reflected by the particular SLA for that transactor) as described herein, or a transactee providing a video file with a low frame rate which may be streamed in fewer packets compared to files of higher frame rate—while for a transactor with a "high" SLA—the transactee offering the fastest and/or highest quality such file may for example be chosen regardless of cost considerations); network connectivity properties of the transactor and/or potential transactees; the number of times the given network request, or a related, prespecified network request has been sent by the gate or otherwise by another, different gate (see subsequent paragraphs herein); the times of previous sending events for the request or a related request; the number of replies received for earlier sending events of such requests, an inventory or supply known to be available to a given transactee which may, e.g., be included in a database stored by the gate in a manner similar to that of Table 1 (for example the maximum, as opposed to the presently measured, communication traffic capacity for a transactee providing the requested video file; in some embodiments, transactees may voluntarily submit such information to the gate in order for it to make destination determination decisions), etc. It is to be understood by those skilled in the art that various alternative rules and combinations of such may be used as well.

A success rate or probability of successfully servicing a specific request or request type may be calculated, for example, for each potential transactee or destination operating a computer which may be determined for a given network request—based on for example the history of network request which may be monitored and recorded in the gate's memory. For example, embodiments of the invention may ask or require the transactor and/or transactee (e.g. via a computing system operated by the transactor) to note, e.g. using a personal computing device, whether or not the requested service has been provided (e.g., if a cardiologist appointment has in fact taken place), and to record or store the answer in an appropriate data structure (such as for example under the "Completed?" field in Table 3). Embodiments may accordingly make use of historical data recorded for a plurality of network requests, for example in order to calculate the probability of a particular transactee successfully servicing a request of a given type. As a non-limiting example, embodiments may search and/or gather all transactions of a given type (e.g., appointment) serviced by a particular transactee (e.g., according to a transactee ID, for example corresponding to Dr. John Doe in Table 1) and calculate a success percentage or score for the relevant request type based on for example Formula 1:

$$S_{Pr\_ID}(T) = \frac{N_c(T)}{N_c(T) + N_i(T)} * 100\% \qquad (1)$$

Where $S_{Pr\_ID}$ (type) is the success rate or percentage of successful servicing of requests of type T (which may be for example "appointment" as in Table 3 herein) for a given transactee or practitioner (which may be described e.g. by a practitioner ID as for example demonstrated in Table 1); $N_c(T)$ is the number of requests of type T which have been "completed" or successfully serviced by the practitioner, and $N_i(T)$ is the number of requests of type T which have not been serviced or completed by the practitioner (for example due to cancelation by the practitioner, or due to failure in providing and/or executing the requested service, and so forth). In some embodiments, input variables for using formula 1 may for example be derived from data structures such as Table 3. In some embodiments, a similar calculation employing a similar formula may be used in order to determine a probability for a desirable reply to be sent by a transactee, which may for example include an offer to service the request fulfilling a plurality of predefined conditions or criteria (such as for example being serviced on the same day in which the request was sent by the transactor, or including a "free cancelation" feature by the transactor, or any other feature and/or benefit which may not explicitly or necessarily be provided be the transactee) based on the history of network requests managed by the gate and serviced by that transactee. Alternative formulas including different parameters and variables may be used in different embodiments of the invention.

Embodiments may allow determining a set and/or subset of destinations for which the probability of the request being serviced successfully, or serviced in a satisfactory manner, is above a predetermined threshold. For example, formulas and data structures such as formula 1 and Table 3 herein may be used to determine success rates per request type for a plurality of transactees (e.g. all potential transactees operating a computer which may be chosen to service the request). Embodiments may then choose or determine a subset of transactees for which success rates are the highest (such as for example the three transactees corresponding to the top three success rates) and send the request to the chosen subset of transactees in order to improve the chance that the request will, in fact, be serviced. Alternative destination determination procedures which may include determining a set and/or subset of destination transactees based on past statistics, historical data/metadata of network requests stored and/or recorded by the gate, calculations of success rates, and corresponding prediction or estimation of future success in servicing a request (e.g. of particular type) may be used in different embodiments of the invention.

Embodiments may further calculate a probability of success, which may be or may include for example a probability for a request (or a request of a given type) being successfully serviced by a set or subset of transactees. A non-limiting example formula for such calculation is illustrated in formula 2:

$$P_s = \frac{S_{Pr\_ID1} + S_{Pr\_ID2} + \ldots S_{Pr\_IDn}}{N_{Pr}} \qquad (2)$$

where $P_S$ is the probability of success, or the overall probability that the network request will in fact be serviced by the set or subset of transactees under consideration; $S_{Pr\_ID1}$, $S_{Pr\_ID2}$, and $S_{Pr\_IDn}$ are the calculated success rates for a first, second, and $n^{th}$ transactees, respectively (which may for example be described by corresponding practitioner IDs); and $N_{Pr}$ is the total number of transactees or practitioners in the set or subset of transactees which may be chosen to service the request.

Thus, in some embodiments of the invention, the determination of destinations for a given network request may comprise or include calculating probability of success (and/or calculating success rates) as discussed herein. In such manner, embodiments may determine a set or subset of destination transactees based on a probability (which may be for example the probability of success calculated by embodiments of the invention) for the corresponding request to be successfully serviced. In some embodiments, the number of destination transactees included in the set or subset may vary based on the calculated probability of success, such that the overall probability of getting adequate service for the corresponding network request satisfies a plurality of predefined conditions or criteria (such as for example being above/below predetermined thresholds). An example procedure which may incorporate such methodology in the context of destination determination by the gate may be, for example:

I. Choose and/or determine a transactee/destination, or a plurality of transactees/destinations, to service the request and add the latter to the set of chosen or determined transactees/destinations.

II. Calculate a probability of success (and e.g. the underlying success rates) for the determined transactees/destinations, for example according to formulas 1-2.

III. If the probability of success is below a predetermined threshold (such as for example 90%), then repeat steps 1-2 to determine or choose an additional transactee/destination, or a plurality of transactees/destinations based on the probability. If the probability of success is equal to or greater than the threshold—then stop (and continue, for example managing the lifecycle of the network request according to the contents of the description herein).

Those skilled in the art may recognize that alternative procedures and/or calculations for ensuring and/or predicting and/or estimating that the probability for a given request to be serviced successfully (or, for that matter, the probability for the servicing of the request to include desirable features) satisfies and/or fulfills predefined conditions or criteria may be used in different embodiments of the invention.

Once such subset is determined, embodiments of the invention may allow routing the request to the determined subset of destinations (e.g., different potential transactees offering video files for the requested movie). Various routing protocols and procedures known in the art may generally be used in different embodiments of the invention as part of sending a given network request to a plurality of selected destinations.

Following the routing of a given requests, embodiments of the invention may send the routed request to one or more destinations over a data network based on the particular route determined for it. The sending of a request may be performed according to various network protocols known in the art. As in the case for determining destination transactee addresses for a given request, the sending of a request may also be performed according to various rules implemented in BREs—e.g., according to measured and/or predicted load-balancing considerations as described herein. In some embodiments, the gate may be configured to send or return the request to the sending address of the transactor (e.g., as performed in request management or destination determination scheme A as described further herein). In some embodiments, the gate may be configured to receive or retrieve a sending address for a given request once the request itself is received and handled by the gate (e.g., in cases where it is not already stored in the gate's memory).

Embodiments of the invention may allow receiving a plurality of replies from the different remote destinations per a given request (replies may be, for example, offers from different transactees including associated details and/or information regarding a medical service requested by the transactor such as possible times for an appointment with a cardiologist, or a frame rate for a video file which may be supplied to service the request). In some embodiments, the request and/or replies for a given request may be stored in a memory unit available to the gate (for example memory 120 in computer system 100) in a manner similar to the storing of transactor or transactee details and various information items, and/or to the storing of network requests and their metadata. Received replies may be associated with information items such as for example an identifier, which may be, for example, a date-and-time of sending/receiving (e.g., based on an appropriate timestamp), a SLA for the corresponding destinations (for example based on their agreement with the service provider operating the gate), and additional information which may be for example fields in a table analogous to Table 1. Replies received for the request may be identified and grouped based on such identifiers or information items, using BREs as known in the art. For example, and as demonstrated regrading determining subsets of transactees or destinations operating a computer to which a given network request may be sent—destinations for which replies were received, as well as replies themselves, may be grouped based on a variety of parameters such as geographic location (e.g., city, district, etc.), cost range (e.g., 300-600 USD), service hours (e.g., 16:00-19:00), and so forth—such that the best servicing options may be chosen by the gate in subsequent stages. In some embodiments, the gate may not possess all the information regarding the subset of service providers or transactees to which the network request was sent. For example the gate may have information regarding service hours for a subset of cardiologists, but have no information regarding service costs—which may only be received per a particular reply for a corresponding service request. In such case, embodiments may indeed benefit from receiving, storing, and processing information items associated with received replies, such that the most desirable destination or transactee may in fact be chosen based on user preferences and SLA (which may, as discussed herein, refer to service costs) in combination with appropriate BREs. Embodiments may thus extract and store reply details and/or information and/or information items in a gate's memory, for example in databases and/or tables analogous to e.g. Tables 1-3. An example for a database including reply information is illustrated in Table 4. Such data and/or database may be used by embodiments of the invention for example in various decision making procedures as demonstrated herein.

TABLE 4

| No. | Reply ID | Transactee ID | Sending time | Time of arrival at gate | Priority level | Request specifications | Satisfaction Score |
|---|---|---|---|---|---|---|---|
| 1. | [4001] | [00101] | 21:23:31 | 22:20:35 | Low | File or link to a file including reply details chosen or specified by transactee | 87.3 |
| 2. | [4002] | [00102] | 23:23:45 | 23:30:01 | High | File or link to a file as above. | 22.1 |
| ... | ... | ... | ... | ... | ... | ... | ... |

Embodiments of the invention may employ various automatic decision making procedures using for example a plurality of BREs and based on for example a plurality of information items. A non-limiting decision making procedure which may be carried out by the gate based on for example transactor SLAs, may be, e.g.:

Procedure I:
1. Receive a network request (e.g., for a medical service such as meeting with a cardiologist) from a given transactor (which may use and/or operate and/or be represented by a computer system connected to a network).
2.i. If the transactor's SLA is low:
   a. Search for possible transactees (which may use and/or operate and/or be represented by a computer system connected to a network) found within a predefined distance.
   b. For each transactee found, calculate score=5d*c, where d is the distance between the transactor's and transactee's locations, and c is the cost associated with the requested service.
   c. Send the request the three destination transactees with the lowest scores.
   d. Choose the first transactee to send a reply, and instruct the transactor to head to the former's address (e.g., as part of an updated reply, as further discussed herein).
2.ii. Alternatively, if the transactor's SLA is high:
   a. Search for the possible transactees found within a predefined distance (which may for example be shorter than the one used in 2.i.a).
   b. For each transactee found, calculate score=10d*c (such that a larger weight is put on distance compared to cost considerations)
   c.1 Send the request to the three destination transactees (which may e.g. correspond or be represented by remote computing systems connected to the network) with the lowest scores (in some cases, the contents of the request sent to the transactees may depend on the SLA of the transactor; if an appointment with a cardiologist is requested, for example, a high SLA may e.g. be interpreted by an appropriate BRE as an indication and/or permission to request for example a cardiologist visit to the transactor's home address, which may be an exclusive service which cannot be trivially booked by transactors having lower SLAs).
   c.2 Alternatively, send the request to a plurality of destination transactees such that the overall probability of getting adequate service is above 90% (see discussion herein regarding the calculation and use of probabilities of success, e.g., based on historical data/metadata for requests which may be stored and/or recorded in the gate).
   d. Respond (see discussion herein regarding automatic responses by the gate) to replies received by chosen transactees with an instruction to provide the requested service, and when one completes servicing the request—instruct the two others to cease working (using the above example, when one cardiologist notifies the gate upon arrival at the transactor's address, the gate may instruct the other two cardiologists to which the request was sent to return to their clinics and confirm payment for the time they invested until receiving the notification under consideration). It should be noted that other example cases, request types, and servicing contexts may be considered in alternative embodiments of the invention. The present example should thus be considered non-limiting.

Some embodiments of the invention may include performing a set of actions or procedure to handle cases of failure (e.g., where no transactee has responded with an offer for example for the requested medical service, or for supplying a video file to service the request by the transactor, which may or may not include a set of constraints or conditions to be enforced using a plurality of BREs as demonstrated herein). Failure as used herein may generally refer to, e.g., a scenario where chosen transactees respond with a negative reply (e.g., of noting that it is unable to service the request); in case no replies are received within a predefined timeframe (e.g., expiration time of a threshold such as 3 seconds for a given request—which may be, for instance, of low SLA); and generally in cases where the request has timed out or according to network congestion effects. Those skilled in the art would recognize that additional sources and scenarios of failure may be considered in different embodiments. A plurality of predefined thresholds, such as a threshold for an expiration time for a particular request during different stages throughout its lifecycle (e.g., before or after the receiving of replies), may be chosen and used, e.g., based on parameters and/or data and/or metadata of a given request. Embodiments of the invention may automatically resend the request to a plurality of additional destinations and/or transactees of the determined subset of the searched set of destinations and/or transactees as described herein. Resending the request may be done for example based on the information stored in the gate's memory (such as transactee or transactor information as described herein), on the processing of replies and processing results as further described herein, and on an error message received for the network request under consideration (which may be for example a notification that the request has timed out). In some other embodiments, the procedures of searching for or determining of destination transactees may be reconducted and/or repeated upon such cases of failure.

Some embodiments of the invention may allow processing a plurality of received replies and associated or accompanying information items, parameters or metadata (for example, file format, audio quality, and frame-rate information for video files offered by different transactees). Processing of replies and their metadata may enable selecting, based on predetermined rules, a particular reply as the target of the network request or transaction (e.g., that offering the highest frame-rate or audio quality, given a high SLA for the request). In some embodiments, the processing of replies may correspond for example to receiving and extracting information items from received replies, as well as organizing and storing the extracted information as a list or table in computer memory (such as memory unit 115 in system 100), in computer memory (such as memory unit 115 in system 100), in computer memory (such as memory unit 115 in system 100), which may be part of a corresponding database—for example in a manner analogous to that demonstrated in Table 1 for transactee details. Various data structures and parameters and/or fields (for example ones referring to network traffic balancing as demonstrated herein) may be used in various embodiments of the invention. In some embodiments, the gate may be configured to extract information from multiple sources, and during different time frames (for example during different stages during the lifecycle of one or more network requests, such as the receiving of a given request by the gate, or the receiving of one or more of the replies of a given request by the gate, or the receiving of one or more of the replies of a given request). Based on predetermined rules or conditions which may be implemented corresponding BREs, embodiments of the invention may allow handling and responding to several replies simultaneously and automatically—that is, without requiring intervention from a user as further explained herein. In some embodiments, the processing of replies may correspond to extracting (using, e.g., a regular-expression-based Unix Shell script as known in the art) a set of parameters or data entries from one or more replies; organizing the data entries in an appropriate data structure (non-limiting examples include: a list, a table, a graph, etc.); performing calculations or manipulations (e.g., arithmetic) on the entries in the resulting structure to produce results according to predefined rules and policies which may include for example calculating a score based on multiple parameters or factors such as: cost per service offer, estimated supply time, and the like (such score may be calculated, e.g., for different replies and corresponding video file offers for servicing the request, where the score may be for example a weighted average involving information regarding the frame rate and/or resolution and/or audio track quality offered in each reply); and producing an output result (e.g., a list of scores for all replies processed, a choice of transactee with the lowest/highest score—assumed to include the preferable alternative for servicing the request). In some embodiments, the gate may be configured to wait for the receiving of a certain number of replies (for example a total number of four offers from cardiologists that may service the user's request) before initiating the processing procedure. In other embodiments, the gate may be configured to wait for a predefined or optimized time window (for example one hour), or until a specific timeslot is reached (e.g., until the end of the day is reached, e.g. by 23:59), before processing received replies. Other constraints on the length and scope of the receiving of replies or processing stages and/or procedures may be employed as well. In some embodiments, the processing of replies by the gate may correspond to selecting or choosing one or more destinations or transactees and including their replies (which may be offers to service the request by the transactor) in an updated reply, which may be prepared by the gate and sent to the transactor. In such manner, the most appropriate reply or offer may be chosen by the transactor based on the updated reply—as further described herein.

Once a processing result has been produced or generated, embodiments of the invention may allow packaging or preparing an updated reply based a plurality of replies received by the gate (e.g., based on the replies processes as described herein); the updated reply may then be sent for example to the transactor's sending address, in order to allow the latter to respond to a particular reply (e.g., to confirm the servicing of the network request by a particular transactee chosen in the processing stage as described herein—such as confirming a particular offer of a video file to be streamed at a predetermined rate and/or quality by such transactee).

In some cases and according to some embodiments of the invention, the updated reply may for example comprise a single reply by a transactee chosen by the gate, e.g., alongside decision making factors used for choosing that particular reply (for example noting that the chosen reply was selected based on minimal geographic distance from the transactor's address, such as for example illustrated in Procedure I.). In some embodiments, the gate may automatically respond to accept the servicing offer provided in a given reply by a given transactee, and note the accepting of the offer in the updated reply sent to the transactor. In some cases, the updated reply may include for example a plurality of potential servicing options and/or offers by one or more transactees (such as e.g. different possible appointment options in different hours of the day, or a selection of different products which may suite the particular network request under consideration, reflecting a plurality of preferences according to the network request or transactor details). Various reply processing procedures may be applied by the gate in the context of preparing the updated reply, which may or may not include all details provided in one or more replies by the set of transactees under consideration. The uniform format of the updated reply may differ in various embodiments of the invention.

In yet another embodiment, the updated reply may include instructions for the transactor, for example in a text file format. Such text file may or may not be human readable, and may for example be further interpreted by a computer program or application installed on, e.g., a computing device used or operated by the transactor (which may or may not be the device used for sending the network request). An example such text file may thus be, for example:

Urep_ID: [45]
   TR_ID: [03021]
   TE_IDs: [00101], [00102]
   Req_ID: [300001]
   Rep_IDs: [4001], [4002]
   Rep_Acc: [4001]
   Rep_Den: [4002]
   Res_ID: [5001], [5002]
   TR_MSG: "Your request for a cardiologist inspection has been accepted by TE_ID[00101], located at [600 E $32^{nd}$ St., Manhattan, NYC]. Please confirm your appointment and attend the address at the time specified by TE_ID[00101]".

In the above example, TR_ID and TE_IDs may be for example transactor and transactee IDs, respectively; Req_ID and Rep_ID may be for example request and reply IDs (e.g., as illustrated in Tables 3-4), respectively; Res_IDs may be for example an identification for responses sent by the gate to the transactees under consideration, e.g., accepting or rejecting servicing offers made by the latter (see discussion herein regarding responses by the gate). Such identification numbers may for example be further interpreted by an application provided by HMO 1, to which the client or transactor belongs to, such that the transactee which offered the service option accepted by the gate may be displayed in the corresponding text message sent to for example the transactor device. It should be noted that alternative updated reply formats may be used in other embodiments of the invention.

In some embodiments, the updated reply may be automatically prepared and sent, for example, as a text file, and/or as a spreadsheet, based on, e.g., information items already gathered and/or stored in the gate (e.g., information already provided by service providers or transactees as demonstrated in Table 1, as well as information drawn or derived from received replies as described herein). In addition to reply processing results, the updated reply may include additional parameters and/or data and/or metadata which may, e.g., provide useful network-related information (for example, such parameters, data or metadata may describe a plurality of replies, of different network requests, of different stages throughout their lifecycle, of routing and/or sending procedures performed, of network activity corresponding to different transactors, transactees or gates, etc.).

In some embodiments, the updated reply may be stalled in the gate's memory for a certain time-frame before its sending (for example it may be stalled for a single hour, or until the end of a business day before sending—depending on whether or not the transactor has responded to one of the replies or offers as further described herein); in some embodiments, the updated reply may be further updated during the time of its stalling (e.g., in cases where the gate is configured to send an updated reply before the ending of a timeframe that has been predefined for the receiving of replies, and where additional relevant replies from transactees have been received and/or processed following the sending of such updated reply). In some cases, the stalling of the preparing and/or the sending of the updated reply may enable the gate to wait (for example for a predefined timeframe) until a preferred reply is received by the gate. The gate may be configured to accept such preferred reply automatically, for example by responding with accepting the servicing offer included in that preferred reply. In this context, a reply may be recognized by the gate as "preferred" according to for example the SLA for the transactor under consideration (which may indicate e.g., high sensitivity to cost considerations as explained herein) as well as according to additional request parameters (such as for example specifying that the cheapest servicing option should be chosen).

Embodiments of the invention may send a plurality of responses to one or more of the destinations from which replies were received based on various information items stored in the gate's memory (which may include or describe the network request under consideration, replies received for it, and the updated reply prepared based on the latter; additional, different network requests, as well as the corresponding replies and updated replies generated for them may also be used). Responses may generally include confirming the receiving of the reply from one or more of the destinations, accepting or rejecting the offer included in a given reply, and canceling the request—as well as a report for the request, which may include one or more of the information items stored in the gate's memory as further described herein. Other types of responses may also be used in different embodiments of the invention.

As demonstrated for requests and replies, a dedicated database may for example be used and/or stored by the gate in order for example to keep track of different updated replies and/or responses sent to, e.g., a plurality of transactors and transactees, which may be using and/or operating and may be represented by a plurality of computer systems connected to a data network. It should be noted that all databases describing requests, replies, updated replies, and responses may be updated in real time (for example periodically, every X minutes; or following every action executed by the gate) in order to incorporate information regarding the gate's activity, as well as activities by the transactor and/or transactees, as for example illustrated in a decision making procedure herein. An example database for monitoring different responses made by the gate may, e.g., be illustrated in Table 5:

TABLE 5

| No. | Response ID | Reply ID | Accept/ Deny | Sending time | Confirmed? | Time of confirmation | Satisfaction Score |
|---|---|---|---|---|---|---|---|
| 1. | [5001] | [4001] | A | 23:43:31 | Y | 00:20:35 | 87.3 |
| 2. | [5002] | [4002] | D | 23:43:45 | Y | 00:30:01 | 22.1 |
| ... | ... | ... | ... | ... | ... | ... | ... |

In the above example, the gate may automatically accept (A) the offer included in reply [4001] and deny (D) or cancel the offer included in reply [4002] by the corresponding transactees (e.g., those also included in Table 1). Such responses may for example be included in an updated reply sent to transactor [03021] included in Table 2, which may be the sender of the corresponding network request (e.g., for an appointment with a cardiologist, as demonstrated herein). The updated reply may for example conform to the updated reply format demonstrated herein. Once sent to the corresponding transactees—which may be, e.g., [00101] and [00102] in Table 1—the transactees may for example receive and confirm the response, thereby committing to provide the requested service. Upon confirmation, the gate may for example update the corresponding field (Confirmed?) in the response database of Table 5, indicating which offers were accepted (e.g., automatically, by the gate, or according to a manual choice by the transactor based on an updated reply) and confirmed by the transactees (Y=response confirmed, N=response not (yet) confirmed). Furthermore, the gate may for example update the database of Table 5 following the execution of the service offer provided by one or more transactees, and e.g. after the transactor has rated the provided service according to his or her overall satisfaction with the result and/or service quality, as for example may be manifested in a Satisfaction Score. The gate may thus monitor the lifecycle of a plurality of requests and replies and use the corresponding data and/or statistics in various decision making protocols as further explained herein. It should be noted that alternative fields and/or formats for databases involved in such monitoring may vary in different embodiments of the invention.

An additional example for a decision making procedure, utilizing e g data and/or statistics included in Tables 1-5, that may be performed by the gate may be for example:
Procedure II:
1. Receive a network request (e.g., for a medical service such as meeting with a cardiologist) from a given transactor which may use and/or operate and/or be represented by a computing system connected to a data network.
2. Search for potential transactees (which may use and/or operate and/or be represented by a plurality of computing systems connected to the network) found within a predefined distance.
3. For each potential transactee found, search a response database (e.g., such as the one demonstrated on Table 5) and calculate an average satisfaction score based on past satisfaction scores associated with responses to replies by the transactee (see corresponding field in Table 5), e.g., according to $$\frac{S_1 + S_2 + \ldots + S_n}{n},$$

where $S^n$ signifies a satisfaction score stored for response n associated with the transactee, and n is the total number of replies by the transactee taken as input for the calculation of an average satisfaction score.

4. Choose the five transactees having the highest calculated average satisfaction scores.
5. Of the five chosen transactees, filter out transactees for which the calculated average satisfaction score is below a predetermined threshold (e.g., 6.0).
    a. If there are no transactees for which the calculated average satisfaction score is above the threshold, then repeat steps 4-5 with a second, lower predetermined threshold (e.g., 5.0).
    b. If there are no transactees for which the calculated average satisfaction score is above the second threshold, then send a text notification to a transactor's device stating that "there are no available options to service the request".
6. Send the network request to the remaining transactees.
7. Wait for replies from the remaining transactees to be received by the gate.
    a. If no reply has been received within a predetermined timeframe (e.g., 2 hours) from the sending time for the request (e.g., as specified in Table 3), then send a text notification to a transactor's device as in 5.b above.
    b. If at least reply has been received within the predetermined timeframe, then proceed to the next step without waiting for additional replies to be received by the gate.
8. Accept the reply including the service option to be provided as soon as possible (for example a reply offering an appointment with a cardiologist taking place within 24 hours form the sending of the request)
9. Wait for a confirmation by the transactee whose reply was accepted.
    a. If no confirmation has been received, within a second predetermined timeframe (e.g., 1 hour), then repeat the preceding step for the reply including the service option to be provided at the $2^{nd}$ closest time period to the time of sending the request (e.g., two days after the latter sending time).
10. Upon the receiving of a confirmation, deny all remaining replies (e.g., send a cancellation message such as "apologies, but a preferred service option for [Response_ID] has already been chosen", where Response_ID is taken for example from a database such as Table 5).
11. Instruct the transactor to attend the address associated with the transactee whose service offer was confirmed. Note that the latter transactee was chosen to service the request.
12. Wait for a notification from the chosen transactee indicating the service has been provided.
13. Ask the transactor (e.g. via a computing system operated by the transactor) to rate his satisfaction with the service provided—e.g., using a satisfaction score such as illustrated in Table 5.
14. Based on the rating by the transactor, update the corresponding databases in the gate's memory—for example a database such as Tables 4-5 which includes satisfaction scores for a plurality of replies and responses, respectively, and Table 1—where the "Rating Score" for each potential transactee or practitioner may be for example an average of all satisfaction scores received (e.g., within another predetermined timeframe such as for example a month) for replies associated with that transactee.

It should be noted that some of the above steps (e.g., 5, 7, 9) in Procedure II may be performed iteratively, using dynamic thresholds and/or timeframes, and that different steps and corresponding calculations and updating of data structures by the gate may be used in different embodiments of the invention.

Some embodiments of the invention may include preparing and sending one or more reports to a plurality of transactee addresses or destinations. Reports may include, for example, information regarding times and contents of some or all of the replies received and/or processed earlier by the gate, as well as parameters, data or metadata describing network activity concerning network requests as disclosed herein, e.g., in the context of calculating network trafficking scores. In addition, reports may include the information associated with the transactees which was collected, used, or processed by the gate or transactor during different stages throughout a given request's lifecycle (for example, the times of receiving of different replies and properties of the different video files offered in them—such as audio quality and format, video resolution and frame rate, and so forth—as well as the locations of transactees providing the replies may be included in a report). In some embodiments, reports may also include details of the transactee chosen and eventually contacted by the transactor; in such case, the transactor may notify the gate after contacting or responding to the transactee of choice (e.g., based on information included in the updated reply by the gate). In some embodiments, different reports may be sent to different transactees according to, e.g., their contact information and/or the contents or metadata associated with the corresponding replies. For instance, a given report including detailed information regarding the receiving of a plurality of replies (e.g., times of sending the replies by all transactees under consideration, their geographic locations, and the like) may be sent to transactees or destinations having a "high" SLA with the organization operating the gate (for example a cardiologist having an appropriate contract with the HMO under consideration) while a less-detailed report may be sent to transactees having a "low" such SLA (e.g., a cardiologist having no such contract, which may for example be contacted by the gate in case no other clinicians are available to service the user's request). Embodiments of the invention may employ a plurality of destination determination or network request management schemes from which a particular scheme may be determined or chosen in order to service a given network request. Generally speaking, such request management schemes may comprise a set of rules which may dictate different stages and actions taken by the gate throughout a given network request's lifecycle (including, for example, storing information items in the gate's memory, determining of one or more potential destinations for the request, returning the request to a sending address, sending of the request to one or more of the destinations, resending of the request to additional destinations, processing one or more replies, generating and sending of an updated reply for the request, and sending of one or more responses to one or more of the destinations, extracting and storing information describing for example each of the aforementioned stages, and the like—as described herein). Thus, a given scheme may correspond to different actions and stages throughout a given request's lifecycle by various information items already stored in the gate's memory. Each of the actions and/or stages may generally be set by one or more of the information items stored in the gate—in accordance with the present disclosure. As noted herein, information stored in gate's memory at a given point in time may for example describe additional, different network requests and replies; the corresponding reports and responses may be included as well. Such information may therefore be combined with appropriate BREs to determine or choose a particular routing scheme for a given network request at any given stage of its lifecycle. Several non-limiting example destination determination or request management schemes are illustrated in FIGS. 2-4, which include a computer data network structure representing the connectivity between transactor 210, gate 220, and the different transactees 230a-c determined for a request by transactor 210—as well as workflows describing example lifecycles (on the right side of each figure) for a network request managed using the destination determination scheme under consideration. Transactor 210, transactees 230a-c, and gate 220 may be or may correspond to a plurality of computer systems (characterized by an architecture such as for example that of system 100) connected to a network as explained herein. Note that transactor 210 and gate 220 may be for example computer systems that may be physically connected, e.g., using a wired connection, while communication between gate 220 and transactees 230a-c may be carried out through a wireless data network. Other networks and connections among different nodes which may be for example transactees, the transactor, and the gate, may be used in different embodiments of the invention (all nodes may for example be computer systems that communicate with one another using a single wireless data network).

One destination determination scheme (referred to as "scheme A" herein) may include, upon receiving a request from a remote computer of a transactor, determining a destination transactee address for the request (based, e.g., on BREs and corresponding rules as described herein); possibly or optionally routing the request to the determined destination (e.g., according to routing methods known in the art); and returning the routed request back to the transactor's computer. The latter may then send or transmit the routed request to its destination according to preceding routing by the gate. Such destination determination scheme may be desirable in cases where the transactor or user may essentially have to directly contact the transactee—for example where a patient has to manually provide information such as medical symptoms to a cardiologist, such that the overall process of servicing the request is not expected to benefit from full-automation. The HMO operating the gate under consideration may therefore configure the latter to execute such destination determination scheme given similar scenarios. Scheme A is illustrated in FIG. 2. It can be seen that gate 220 may receive a request by transactor 210, determine a destination for the request (which may be for example transactee 2 230b as illustrated in the workflow for the scheme at hand), and then send the request back to transactor 210—which may, in turn, send the request to the destination determined for it. A reply for the request may then be sent back from the chosen destination (e.g., transactee 2 230b) to transactor 210, which may then respond accordingly (e.g., choosing to accept the offer for servicing the request). In this context, as well as in additional figures considered in this document, transactor 210 and transactees 230a-c may be or may operate computers such as for example system 100 as described herein. Gate 220, transactor 210 and transactees 230a-c may accordingly be connected via a data network 200, for example as described herein.

In some embodiments of the invention, replies received for requests sent using scheme A may be received by the transactor's computing device, which may then send them over to the gate for further servicing actions (e.g., processing and/or documentation of reply contents and metadata). In other embodiments, the transactor's computing device may not further involve the gate in the servicing of requests once, e.g., in the case of a reply has been received. In such case, all additional actions (e.g., responding to that reply) may still be taken or performed by the transactor's computing device.

Another example destination determination scheme ("scheme B" herein) may include, following the receiving of a request from a remote computer of a transactor, the determining of a specific destination transactee address for the request, and the routing of the request to the determined destination: sending the request to the destination; receiving a reply from the destination; if the reply is satisfactory (e.g., if it conforms to rules implemented in a corresponding BRE) then sending it to the transactor (e.g., immediately, without waiting for additional replies); in the contrary case, embodiments may determine a different, alternative destination transactee address for the request; and routing and/or sending the request to that alternative destination. Such routing scheme may be preferred, for example, in cases where a single reply from a selected destination is expected to conform to the rules and preferences as implemented in BREs—namely in cases where multiple replies from a plurality of transactees are not assumed to be needed in order for the request to be serviced within a predetermined timeframe. For example, an HMO gate may be configured to manage network requests for a routine appointment at a cardiologist's clinic such that, within a timeframe of 24 hours, the request is to be sent to a single transactee which may be a particular cardiologist clinic, and wait for a reply which may indicate whether the transactee under consideration would or would not be able to service the request—namely to schedule the requested appointment. In case no reply was received within one hour, the gate may be configured to determine a new destination, and/or route, and/or send the request to another, different transactee and accordingly wait yet another hour for a reply. Additional destinations or transactees may be contacted in this manner, until the 24 hour limit is reached; the gate may then for example be configured to either notify the transactor of a failure to manage the request, or for example change the destination determination scheme to scheme C which allows sending the request to a plurality of transactees and accordingly receiving a plurality of replies as described herein and may offer a faster workflow compared to sending the request to a single transactee at a time. Different predetermined timeframes, as well as additional conditions and setting as illustrated herein may be used in various embodiments of the invention.

Scheme B is illustrated in FIG. 3. It can be seen that gate 220 may receive a request by transactor 210, determine a destination for the request (e.g., transactee 2 230b similarly to the discussion regarding scheme A herein and as illustrated in workflow for the scheme at hand), and then send the request directly to the destination determined for it. A reply for the request may then be sent back from the chosen destination (e.g., transactee 2 230b) to gate 220, which may then forward it to transactor 210. The latter may subsequently choose an appropriate response (e.g., accepting the offer by transactee 2 230b).

A third example destination determination scheme ("scheme C" herein) may, in order to send the request to a plurality of destinations or transactees and accordingly receive a plurality of replies, include a set or subset of steps as outlined herein, e.g.: receiving a computer network request from a transactor (e.g., corresponding to or represented by a remote computer); searching for a plurality of potential remote destinations to service the request; determining a subset of two or more remote destinations to service the request; routing the request to multiple transactee sites; sending the routed request to the transactee sites over a data network; receiving replies from different transactees; processing received replies; preparing and sending an updated reply to the transactor; and preparing and sending reports to transactees, describing the receiving of their replies. Each step may be performed according to different BREs and corresponding rules. Such destination determination and management scheme may prove useful, e.g., in cases where a quick reply is needed. For example, in case of a heart emergency, a HMO's gate (which may be contacted automatically for example based on a notification sent by a heart monitoring device detecting a heart failure as known in the art) may send a request for emergency care to a plurality of destinations, which may be for example emergency care units. In such case, the gate may be configured to wait 3.0 seconds for replies to be received, and subsequently send an updated reply to the user's device. If no replies were received, however, the gate may be configured to send the request to a plurality of different transactees (e.g., by first searching for such transactees in a database such as the one illustrated in Table 1, determining a subset of transactees to which the request is to be sent, and routing the request accordingly) and this time wait for 1.0 seconds before sending an updated reply to the transactor and automatically responding and/or accepting an offer received from one of the transactees (e.g., in order for the user to receive treatment as soon as possible).

Scheme C is illustrated in FIG. 4. It can be seen that gate 220 may receive a request by transactor 210, determine a plurality of destinations for the request (e.g., transactee 1 230*a*, transactee 2 230*b*, and transactee 3 230*c* as illustrated in the corresponding workflow included in the left side of the figure), and then for example send the request directly to the destinations determined for it. Replies for the request may then be sent back from the chosen destinations (e.g., transactee 1 230*a* and transactee 2 230*b*) to gate 220, which may then process the replies and send an updated reply to transactor 210. The latter may be configured, for example using appropriate BREs and corresponding criteria and/or conditions, to choose an appropriate response (e.g., accepting one of the offers by transactee 1 230*a* and transactee 2 230*b*), or for example wait for a predetermined timeframe until a reply from yet another destination is received (for example a transactee that has been pre-determined as the preferred option to service the request—which may be, e.g., transactee 3 230*c*), or until a predefined number of replies are received by gate 220 (e.g., a total of three replies). Once the corresponding criteria and/or conditions are fulfilled, gate 220 may be configured to send responses to a plurality of destinations from which replies were received, for example without further intervention by transactor 210 (e.g., one response rejecting the offer by transactee 1 230*a*, and a second response accepting the offer by transactee 3 230*c*). In some embodiments, however, gate 220 may also be configured to manage requests by transactor 210 such that, e.g., some replies by transactees determined for the request (for example one or more of transactee 1 230*a*, transactee 2 230*b*, and transactee 3 230*c*) may be sent directly to transactor 210 without further mediation by gate 220. In other embodiments, gate 220 may be configured to manage requests such that replies from the latter transactees may be sent to both gate 220 and transactor 210. Additional configurations may be used in other embodiments of the invention.

In some embodiments of the invention, a particular destination determination scheme may be chosen for a given network request received by the gate based on request information, parameters, data or metadata—in accordance with the above disclosure. For example, using an appropriate BRE and based on information items collected at different stages throughout a network request's lifecycle as described herein, the gate may choose to use scheme A for network requests of low SLA, and scheme B for those of high SLA. As a different example, rules employed in BREs used for choosing a destination determination scheme for a network request may include constraints and/or conditions involving its expiration time or requested time for response: in such manner, a request for which replies are to be received within 1 second may be managed by the gate using scheme B, while requests for which replies are to be received within 5 seconds may be managed using scheme C. Additional embodiments of the invention may combine different rules and constraints, for example on both SLA and expiration time of a given request (e.g., for a low SLA and expiration time at a threshold of for example 1 second, use scheme B; for a high SLA and similar expiration date use scheme C). Needless to say, different examples and cases may call for different rules and constraints—thus, particular examples used herein should be seen as non-limiting. The choosing and/or determining and/or changing of a network scheme for a network request may be based on request parameters, data or metadata, such that different destination determination workflows (e.g., composed of various stages of schemes A-C described herein) may be chosen for, or matched with different requests. In such manner, embodiments of the invention may allow optimizing the gate's performance, capacity, and processing capabilities—for example based on network load-balancing considerations or predictions for a given request based on its parameters, data, or metadata. As a non-limiting example, a request by an HMO client may be managed using destination determination scheme A in case where the latter (e.g., the transactee) would have to manually interact with a service provider (e.g., verbally describe his or her symptoms to a cardiologist, such that the interaction with the clinician might not at all benefit from automation); scheme B may be chosen in case where a particular destination is known or assumed to be able to successfully service the request (e.g., a cardiologist clinic known to be open and available for communication at certain service hours) and scheme C may be chosen in cases where a quick reply may be desirable and/or where it is not clear what transactee would constitute the best service option (for example in case there are three cardiologist clinics within 1 km away from the transactor's residence, and where none of them is pre-known to be available to provide the requested service; the gate may thus send requests to all three clinics and attempt to receive and accept a corresponding offer as quickly as possible). In some embodiments, the gate may be configured to first attempt using the same destination determination schemes and/or chosen transactees that have successfully serviced past network requests, for example by the same transactor (for example the gate may choose, by default, the same cardiologist clinic that had already serviced past requests by the transactor, unless it is known not to provide the particular service requested at present).

In some embodiments, a chosen network scheme may be changed, and a different scheme may be chosen "on the fly" for a given request at a given point in time (e.g., upon the case of failure). For example, destination determination scheme B may initially be chosen for a given request of a low SLA and an expiration time of a threshold of for example 3 seconds; however, if the transactee chosen as a destination fails to provide a reply by the time 2.1 seconds have passed (i.e., there are 0.9 seconds remaining until the request expires), the gate may change the destination determination scheme for the request to scheme A and return it to the transactor's sending address as disclosed herein. Some embodiments may allow changing a request management or destination determination scheme several times, e.g., upon subsequent cases of failure for the same request. Additional criteria or conditions for choosing and/or changing a request management or destination determination scheme for a given request—based e.g., on information items stored in the gate's memory as described herein—may also be used and, for example, implemented in appropriate BREs as part of different embodiments of the invention.

Figure 5:
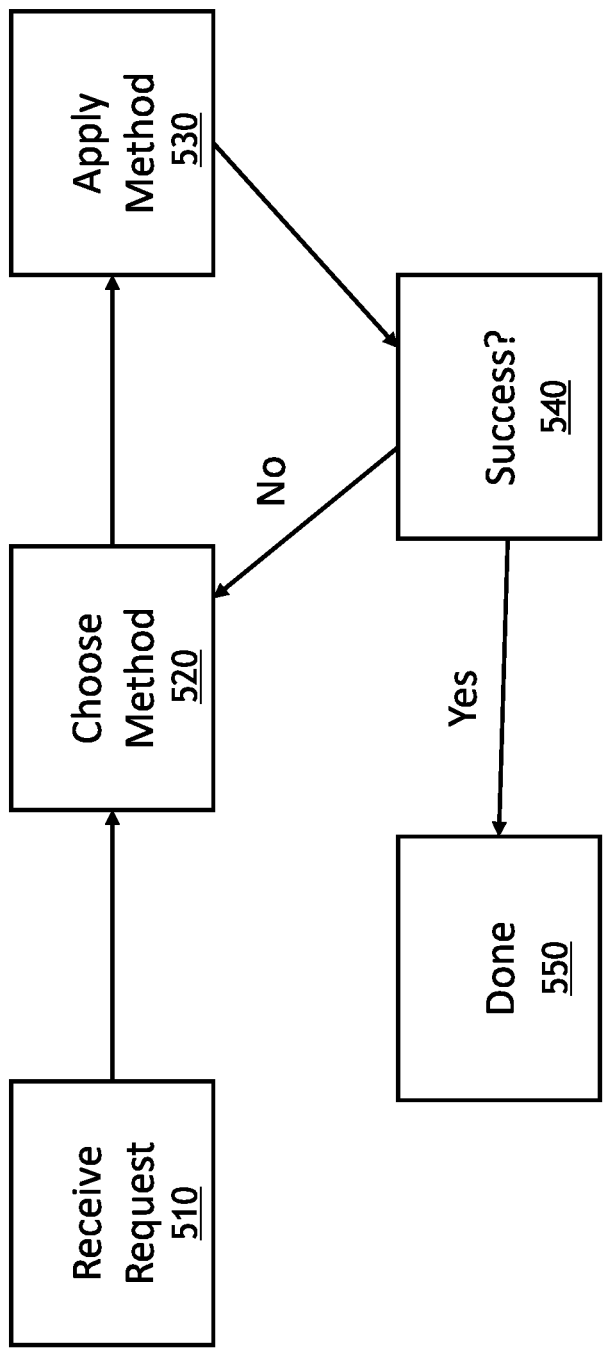
FIG. 5 is a flow diagram illustrating a procedure of choosing or changing a destination determination method according to some embodiments of the present invention.

FIG. 5 is a flow diagram illustrating a procedure of choosing or changing a destination determination method according to some embodiments of the present invention. In step 510 embodiments of the present invention may receive a network request—e.g., by a user or transactor operating a computing system as described herein. Embodiments may then choose a particular destination determination method or scheme which may be used to manage the request, as well as its associated replies and responses, throughout its lifecycle (for example one of destination determination schemes A-C illustrated in FIGS. 2-4; step 520). The method or scheme chosen may then be applied (for example according to different workflows and/or steps outlined herein for schemes A-C), in combination with appropriate BREs, such that the request is sent to, e.g., a plurality of destinations which may be or may operate computing systems as described herein and may successfully service the request (step 530). Embodiments may then determine whether the present destination determination method or scheme is successful, or whether it should be changed (step 540). In a case of failure, e.g., where no reply or offer from either destination was received (for example within a predefined timeframe or time window), embodiments may once again choose the method or scheme to be used from that point to manage the lifecycle of the request under consideration (e.g., changing for example from scheme B to scheme C, thus resending the request to a plurality of different destinations; back to step 520). In case of success, however, embodiments may cease to manage the request and its associated replies and responses (e.g., in case a desirable offer by a transactee has been received and a response by the transactor has been sent to accept the offer, such that the servicing process is done or complete; step 550).

Embodiments of the invention may monitor a plurality of stages throughout a given network request's lifecycle, and thereby collect and organize parameters and/or data and/or metadata describing the history of different network requests and corresponding replies. Monitoring data and/or metadata may be organized in different formats, e.g., as a list, a table, or a graph. Other appropriate data structures may also be used for this purpose. In some embodiments, a plurality of data and metadata (such as for example a plurality of request history data, e.g. as illustrated in Table 3) may be further processed and used for building a statistical model in order to predict and organize future network traffic and additional communication patterns of network requests. While calculating and/or using success rates and/or probabilities in the context of destination determination has been demonstrated herein (e.g. for choosing a set or subset of transactees being most likely to successfully service the request), those skilled in the art would recognize that similar calculations may be used in combination with different input data in order to choose a set or subset of destination transactees which may be characterized or possess a plurality of desirable features. Non-limiting examples of such features may include, e.g., successfully servicing a request (such as e.g. of a given type) within a given timeframe; servicing the request in an exceptionally high-quality manner (which may for example be reflected in Rating Scores such as for example demonstrated in Table 1, which may e.g. be provided manually by transactors once their correspondence or interaction with a transactee or service provider has ended); and so forth. Alternative request history data and/or information, and desirable features that may be reflected and/or correlated with such data, may be used as part of building statistical models and using such models in the context of destination determination in different embodiments of the invention.

Generally speaking, embodiments of the invention may employ workflow and/or algorithm composed of different stages and/or principles as outlined herein (e.g., for schemes A-C). A few example algorithms are descried herein. However, those skilled in the art would recognize that the examples used herein are non-limiting, and that various alternative workflows may be used in other embodiments of the invention—in accordance with the present disclosure.

Figure 6:
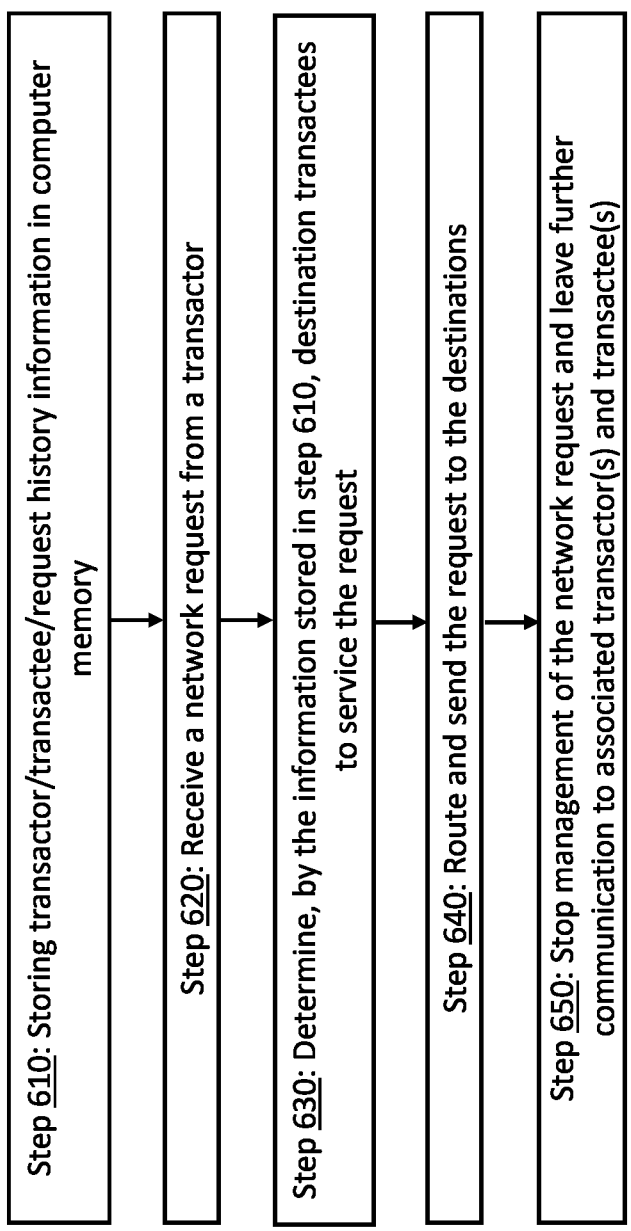
FIG. 6 is a flow diagram illustrating a simple destination determination method according to some embodiments of the present invention.

FIG. 6 is a flow diagram illustrating a simple destination determination method according to some embodiments of the present invention. In step 610, a gate (which may include a computer system such as system 100 as described herein) may store information items describing plurality of transactors or senders and potential remote destinations or transactees which may be chosen to service network requests, as well as information regarding past requests managed by the gate or the history of such requests (e.g., different stages throughout their lifecycle, such as replies received for different requests, responses sent for the replies, times of sending and receiving the latter, and so forth). Such information items may be stored and organized, for example, as a database in computer memory 115 as described herein. The gate may then receive a network request by a given transactor or potential sender (step 620), and accordingly determine a subset of destination transactees to service the request based on the stored information (step 630). The gate may then route the request to the destinations determined for it as known in the art and send the request (step 640), such that it may for example be further managed according to one of the schemes disclosed herein. In step 650, the gate may stop or cease to manage the network request under consideration, and leave further communication to the users under consideration (e.g., a given transactor and chosen transactee(s)) which may communicate over the network without further intervention or involvement from the gate (for example once a particular reply or offer by a transactee has been accepted by the transactor, and confirmed by the transactee or destination; other cases may be considered in different embodiments of the invention).

In the description and claims of the present application, each of the verbs, "comprise", "include" and "have", and conjugates thereof, are used to indicate that the object or objects of the verb are not necessarily a complete listing of components, elements or parts of the subject or subjects of the verb. Unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of an embodiment as described. In addition, the word "or" is considered to be the inclusive "or" rather than the exclusive or, and indicates at least one of, or any combination of items it conjoins.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In detailed description, some features or elements described with respect to one embodiment or flowchart can be combined with or used with features or elements described with respect to other embodiments.

Although embodiments of the invention are not limited in this regard, discussions utilizing terms such as, for example, "processing," "computing," "calculating," "determining," "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes.

The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

Descriptions of embodiments of the invention in the present application are provided by way of example and are not intended to limit the scope of the invention. The described embodiments comprise different features, not all of which are required in all embodiments. Embodiments comprising different combinations of features noted in the described embodiments, will occur to a person having ordinary skill in the art. Some elements described with respect to one embodiment may be combined with features or elements described with respect to other embodiments. The scope of the invention is limited only by the claims.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

The invention claimed is:

1. A method of destination determination for network requests, the method comprising:
   storing, in computer memory, a plurality of information items describing one or more potential senders of network requests and at least one of: one or more computer network requests, one or more historical details associated with the one or more computer network requests, and one or more potential remote destinations for network requests;
   receiving a given network request from one of the potential senders;
   determining, by a computer processor, a subset of two or more of the potential destinations to service the request based on one or more of the stored information items, wherein the determining of one or more of the potential destinations comprises calculating a probability of success for servicing the request by one or more of potential destinations, and if the calculated probability is below a predetermined threshold, choosing one or more additional destinations to service the request;
   waiting for a predefined timeframe for one or more replies to the request from one or more of the determined destinations;
   receiving one or more of the replies each reply from a remote destination; and
   selecting, by the processor, a target for the request based on organizing a set of parameters in a database, the parameters extracted from one or more of the replies.

2. The method of claim 1, comprising sending the request to one or more of the destinations over a data network; and sending, based on one or more of the replies, an updated reply for the request.

3. The method of claim 2, comprising extracting, by the processor, a plurality of information items from at least one of: one or more network requests, and one or more of the replies;
   storing the extracted information items in computer memory; and
   processing, by the processor, one or more of the replies, wherein the processing comprises selecting one or more of the destinations, and wherein the updated reply includes one or more replies from the selected destinations.

4. The method of claim 3, comprising resending the request to one or more of the destinations based on at least one of: one or more of the stored information items, the processing of one or more of the replies, and an error message.

5. The method of claim 3, comprising sending one or more responses to one or more of the destinations, based on at least one of: the request, the one or more replies, the updated reply, and one or more of the stored information items.

6. The method of claim 5, wherein at least one of: the receiving a network request, the determining of the one or more destinations, the routing of the request, the sending of the request, the sending of the updated reply, and the sending of one or more of the responses is set by one or more of the stored information items.

7. The method of claim 6, wherein the one or more of the stored information items describes at least one of: one or more additional, different network requests, one or more replies, one or more reports, and one or more responses.

8. The method of claim 6, wherein one or more of the responses include at least one of: confirming the receiving of the reply from one or more of the destinations, canceling the request, and a report for the request, the report including one or more of the stored information items.

9. A method of choosing a scheme of destination determination for a network request, the method comprising:
   storing, in computer memory, a plurality of information items describing one or more potential senders of network requests and at least one of: one or more computer network requests, one or more historical details associated with the one or more computer network requests, one or more potential remote destinations for network requests, one or more replies to network requests, and one or more responses sent to one or more remote destinations; and choosing, by a computer processor, from a plurality of destination determination schemes, a destination determination scheme for a given request based on one or more of the stored information items, wherein each of the schemes comprises a set of rules for at least one of: returning the request to a sending address, and resending of the request to one or more additional destinations.

10. A system for determining destinations for network requests, the system comprising:
a computer comprising a processor and a memory, wherein the processor is to:
store a plurality of information items describing one or more potential senders of network requests and at least one of: one or more computer network requests, one or more historical details associated with the one or more computer network requests, and one or more potential remote destinations for network requests;
receive a given network request from one of the potential senders;
determine a subset of two or more of the potential destinations to service the request based on one or more of the stored information items, wherein the determining of one or more of the potential destinations comprises calculating a probability of success for servicing the request by one or more of potential destinations, and if the calculated probability is below a predetermined threshold, choosing one or more additional destinations to service the request;
wait for a predefined timeframe for one or more replies to the request from one or more of the determined destinations;
receive one or more of the replies each reply from a remote destination; and
select a target for the request based on organizing a set of parameters in a database, the parameters extracted from one or more of the replies.

11. The system of claim 10, wherein the processor is to:
send the request to one or more of the destinations over a data network; and
send, based on one or more of the replies, an updated reply for the request.

12. The system of claim 11, wherein the processor is to:
extract a plurality of information items from at least one of: one or more network requests, and one or more of the replies;
store the extracted information items in computer memory;
process one or more of the replies, wherein the processing comprises selecting one or more of the destinations, and wherein the updated reply includes one or more replies from the selected destinations.

13. The system of claim 12, wherein the processor is to:
resend the request to one or more of the destinations based on at least one of: one or more of the stored information items, the processing of one or more of the replies, and an error message.

14. The system of claim 12, wherein the processor is to:
send one or more responses to one or more of the destinations, based on at least one of: the request, the one or more replies, the updated reply, and one or more of the stored information items.

15. The system of claim 14, wherein at least one of: the receiving a network request, the determining of the one or more destinations, the routing of the request, the sending of the request, the sending of the updated reply, and the sending of one or more of the responses is set by one or more of the stored information items.

16. The system of claim 15, wherein the one or more of the stored information items in computer memory describes at least one of: one or more additional, different network requests, one or more replies, one or more reports, and one or more responses.

17. The system of claim 15, wherein one or more of the responses include at least one of: confirming the receiving of the reply from one or more of the destinations, canceling the request, and a report for the request, the report including one or more of the stored information items.

18. A system for choosing a scheme of destination determination for a network request, the system comprising:
a computer comprising a processor and a memory, wherein the processor is to:
store a plurality of information items describing one or more potential senders of network requests and at least one of: one or more computer network requests, one or more historical details associated with the one or more computer network requests, one or more potential remote destinations for network requests, one or more replies to network requests, and one or more responses sent to one or more remote destinations; and
choose from a plurality of destination determination schemes, a destination determination scheme for a given request based on one or more of the stored information items, wherein each of the schemes comprises a set of rules for at least one of: returning the request to a sending address, and resending of the request to one or more additional destinations.

* * * * *